United States Patent
Sugimoto

(10) Patent No.: US 9,659,787 B2
(45) Date of Patent: May 23, 2017

(54) HIGH-PURITY 2-FLUOROBUTANE

(71) Applicant: ZEON CORPORATION, Tokyo (JP)

(72) Inventor: Tatsuya Sugimoto, Tokyo (JP)

(73) Assignee: ZEON CORPORATION, Tokyo (JP)

( * ) Notice: Subject to any disclaimer, the term of this patent is extended or adjusted under 35 U.S.C. 154(b) by 0 days.

(21) Appl. No.: 14/773,043

(22) PCT Filed: Mar. 6, 2014

(86) PCT No.: PCT/JP2014/055778
§ 371 (c)(1),
(2) Date: Sep. 4, 2015

(87) PCT Pub. No.: WO2014/136877
PCT Pub. Date: Sep. 12, 2014

(65) Prior Publication Data
US 2016/0016869 A1    Jan. 21, 2016

(30) Foreign Application Priority Data

Mar. 7, 2013 (JP) ................................. 2013-045131

(51) Int. Cl.
| | |
|---|---|
| *H01L 21/311* | (2006.01) |
| *H01L 21/3065* | (2006.01) |
| *H01L 21/3213* | (2006.01) |
| *C09K 13/00* | (2006.01) |
| *C09K 13/08* | (2006.01) |
| *C07C 19/08* | (2006.01) |

(52) U.S. Cl.
CPC ........ *H01L 21/31116* (2013.01); *C07C 19/08* (2013.01); *C09K 13/00* (2013.01); *C09K 13/08* (2013.01); *H01L 21/3065* (2013.01); *H01L 21/32136* (2013.01); *H01L 21/32137* (2013.01)

(58) Field of Classification Search
None
See application file for complete search history.

(56) References Cited

U.S. PATENT DOCUMENTS

| | | | |
|---|---|---|---|
| 2,550,953 A | | 5/1951 | Barrick et al. |
| 4,049,728 A | | 9/1977 | Kraus et al. |
| 5,718,807 A | | 2/1998 | Miler et al. |
| 5,780,672 A | | 7/1998 | Pasenok et al. |
| 2011/0068086 A1* | | 3/2011 | Suzuki .............. H01L 21/31116 216/67 |

FOREIGN PATENT DOCUMENTS

| | | | | |
|---|---|---|---|---|
| JP | 59-46251 A | | 3/1984 | |
| JP | 9-48741 A | | 2/1997 | |
| JP | 10-506107 A | | 6/1998 | |
| JP | 2009-013101 | * | 1/2009 | ........... C07C 17/386 |
| JP | 2009-13101 A | | 1/2009 | |
| JP | 2009-292749 A | | 12/2009 | |
| JP | 2013-95669 A | | 5/2013 | |
| JP | 2014-24785 A | | 2/2014 | |
| WO | 2009/123038 A1 | | 10/2009 | |

OTHER PUBLICATIONS

S. Laly et al., Anal. Chem. vol. 68, year 1996, pp. 4312-4315.*
Translation of Written Opinion dated May 13, 2014, issued in counterpart International Application No. PCT/JP2014/055778 (8 pages).
International Search Report dated May 13, 2014, issued in counterpart Application No. PCT/JP2014/055778 (2 pages).
Olah, G.A. et al, "Synthetic Methods and Reactions. 63. Pyridinium Poly(hydrogen fluoride) (30% Pyridine-70% Hydrogen Fluoride): A Convenient Reagent for Organic Fluorination Reactions", Journal of Organic Chemistry, Oct. 1979, vol. 44, No. 22, pp. 3872-3881. (10 pages).
Extended (supplementary) European Search Report dated Sep. 16, 2016, issued in counterpart Application No. 14759957.5. (9 pages).

* cited by examiner

*Primary Examiner* — Jiong-Ping Lu
(74) *Attorney, Agent, or Firm* — Westerman, Hattori, Daniels & Adrian, LLP

(57) ABSTRACT

The present invention is a high-purity 2-fluorobutane having a purity of 99.9 vol % or more and a butene content of 1,000 ppm by volume or less, and a method for using the high-purity 2-fluorobutane as a dry etching gas. According to the present invention, a high-purity 2-fluorobutane that is suitable as a plasma reaction gas for semiconductors is provided.

3 Claims, No Drawings

HIGH-PURITY 2-FLUOROBUTANE

TECHNICAL FIELD

The present invention relates to high-purity 2-fluorobutane that may be useful as a plasma etching gas or a CVD gas that is used when producing a semiconductor device by utilizing a plasma reaction, a raw material for producing a fluorine-containing medicine intermediate, and a hydrofluorocarbon-based solvent.

BACKGROUND ART

In recent years, semiconductor production technology that achieves further miniaturization has been developed, and a line width of 20 nm or 10 nm has been used for a leading-edge process. The degree of difficulty in processing has increased along with miniaturization, and various techniques are currently under development using various approaches (e.g., materials, devices, and processing methods).

Patent Document 1 discloses that a saturated fluorohydrocarbon (A) represented by $C_xH_yF_z$ (wherein x is 3, 4, or 5, and y and z are independently a positive integer, provided that y>z) exhibits performance better than that of monofluoromethane that is used for etching a silicon nitride film.

Patent Document 2 discloses that 2-fluorobutane was obtained in a yield of 46% by reacting N,N'-diethyl-3-oxomethyltrifluoropropylamine (fluorinating agent) with 2-butanol. Patent Document 3 discloses that 2-fluorobutane was obtained in a yield of 68% by reacting triethylammoniumhexafluorocyclobutane (fluorinating agent) with 2-butanol. Patent Document 4 discloses that sec-butyl fluoride was produced by bringing sulfur hexafluoride into contact with a sec-butyllithium cyclohexane/n-hexane solution. Patent Document 5 discloses that 2-fluorobutane was obtained by hydrogenating 2-fluorobutadiene in the presence of a catalyst.

RELATED-ART DOCUMENT

Patent Document

Patent Document 1: WO2009/123038
Patent Document 2: JP-A-59-46251
Patent Document 3: JP-A-9-48741
Patent Document 4: JP-A-2009-292749
Patent Document 5: U.S. Pat. No. 2,550,953

SUMMARY OF THE INVENTION

Technical Problem

The inventor of the invention used 2-fluorobutane obtained using the above methods as a gas for selectively dry-etching a silicon nitride film formed on silicon or a silicon oxide film. However, a large amount of hydrocarbon-based deposits were produced, and etching stopped.

An object of the invention is to provide 2-fluorobutane that is suitable as a plasma reaction gas, and prevents the production of hydrocarbon-based deposits even when used as a dry etching gas.

Solution to Problem

The inventor conducted studies regarding the reason why the above phenomenon (i.e., a large amount of hydrocarbon-based deposits are produced, and etching stops) occurs when 2-fluorobutane obtained using the above methods is used. As a result, the inventor found that the above phenomenon occurs when 2-fluorobutane includes butene as impurities in a ratio equal to or higher than a given value. This finding has led to the completion of the invention.

Several aspects of the invention provide the following high-purity 2-fluorobutane (see (1) to (4)) and method for using high-purity 2-fluorobutane (see (5)).

(1) High-purity 2-fluorobutane having a purity of 99.9 vol % or more and a butene content of 1.000 ppm by volume or less.
(2) The high-purity 2-fluorobutane according to (1), the high-purity 2-fluorobutane having a nitrogen content of 100 ppm by volume and an oxygen content of 50 ppm by volume or less.
(3) The high-purity 2-fluorobutane according to (1), the high-purity 2-fluorobutane having a water content of 50 ppm by volume or less.
(4) The high-purity 2-fluorobutane according to (1), the high-purity 2-fluorobutane including microparticles having a size of 0.1μm or more in a number equal to or less than 50 per ml.
(5) A method for using the high- purity 2-fluorobutane according to (1) as a dry etching gas.

DESCRIPTION OF EMBODIMENTS

The embodiments of the invention are described in detail below.
High-purity 2-fluorobutane 2-Fluorobutane according to one embodiment of the invention has a purity of 99.9 wt % by volume or more and a butene content of 1,000 ppm by volume or less.

Note that the term "butene" used herein is a generic name for 1-butene, 2-butene ((E)-2-butene and (Z)-2-butene), and isobutene (hereinafter may be collectively referred to as "butenes"). One or more types of butenes present in the 2-fluorobutane are impurities.

The purity of the 2-fluorobutane and the butene content in the 2-fluorobutane refer to values calculated from the peak area determined by gas chromatography using a flame ionization detector (FID).

The butenes may be identified by gas chromatography-mass spectrometry.

The nitrogen content aid the oxygen content in the 2-fluorobutane refer to values determined by gas chromatography using a thermal conductivity detector (TCD).

The water content in the 2-fluorobutane refers to a value determined by FT-IR.

The 2-fluorobutane according to one embodiment of the invention is obtained by subjecting crude 2-fluorobutane produced using a known production method (e.g., a method that fluorinates 2-butanol (raw material) using a fluorinating agent, or a method that treats 2-bromobutane with an alkali metal fluoride (e.g., potassium fluoride or cesium fluoride)) to purification by distillation.

Specific examples of the method that fluorinates 2-butanol (raw material) using a fluorinating agent to obtain 2-fluorobutane include the method described in Journal of Organic Chemistry. Vol. 44, 3872 (1979), and the method described in Bulletin of the Chemical Society of Japan, Vol. 52, 3377 (1979). The method described in Journal of Organic Chemistry, Vol. 44, 3872 (1979) fluorinates 2-butanol (raw material) using a poly(hydrogen fluoride) pyridine complex as the fluorinating agent, and the method described in Bulletin of the Chemical Society of Japan, Vol. 52, 3377 (1979) fluorinates 2-butanol (raw material) using N,N'-diethylaminohexafluoropropane (prepared from hexafluoropropene and diethylamine) as the fluorinating agent.

The crude 2-fluorobutane produced using the above met the above method or the like is subjected to purification by distillation (rectification) or the like to remove organic impurities including butenes.

A rectifying column is used when removing organic impurities by subjecting crude 2-fluorobutane to purification by distillation. A rectifying column having an appropriate number of theoretical plates is used in order to efficiently separate 2-fluorobutane (boiling point: 24 to 25° C.) from butenes (1-butene (boiling point: −6.3° C.), (E)-2-butene (boiling point: 0.9° C.), and (Z)-2-butene (boiling point: 3.7° C.). The number of theoretical plates is normally about 10 to 50, and preferably about 20 to 50. Since the boiling point of these butenes is equal to or less than room temperature, the efficiency of separation from the target 2-fluorobutane may apparently deteriorate due to a vaporization phenomenon within a fraction extraction line of the rectifying column. Therefore, it is preferable to sufficiently cool the fraction extraction line and a first fraction storage container.

The butene content can be reduced to 1.000 ppm by volume or less, and preferably 500 ppm by volume or less by rectifying the crude 2-fluorobutane.

The rectification pressure (gauge pressure) is normally set to a value between normal pressure (1 atmosphere) and 10 atmospheres, and preferably set to a value between normal pressure and about 5 atmospheres.

The ratio of the reflux rate to the distillate rate (hereinafter may be referred to as "reflux ratio") is preferably set to 30:1 or more in order to efficiently separate the butenes that easily gasify. If the reflux ratio is too low, it may be difficult to efficiently separate the butenes, and sufficiently increase the purity of 2-fluorobutane. Moreover, the amount of the first fraction may increase, and the amount of 2-fluorobutane (collected as a product) may decrease. If the reflux ratio is too high, collection (per extraction) may take time, and the rectification time may increase. As a result, productivity may deteriorate.

A batch-wise purification method or a continuous purification method may be used. A batch-wise purification method is preferably used when the production volume is small. When the production volume is large, a continuous purification method that utilizes several rectifying columns is preferably used. An extractive distillation operation that utilizes an extraction solvent may be performed in combination with rectification.

When the reaction conversion ratio is low, and it is necessary to collect the raw material, for example, a stepwise distillation operation (that separates the raw material compound by the first distillation, and separates the butenes (impurities) by the second distillation, for example) may be performed depending on the reaction used to produce 2-fluorobutane. In this case, it is preferable to set the reflux ratio to 40:1 or more.

Nitrogen and oxygen included in 2-fluorobutane may be remove be removed by removing the butenes by rectification using a Group 0 gas (inert gas), or subjecting 2-fluorobutane to simple distillation, and extracting a fraction, for example.

When using the latter method, the nitrogen content and the oxygen content in 2-fluorobutane that remains in the still can be reduced by subjecting 2-fluorobutane to simple distillation, and removing nitrogen and oxygen together with 2-fluorobutane. The nitrogen content and the oxygen content in 2-fluorobutane that is extracted are preferably 20 to 50 wt %, and more preferably 30 to 40 wt %, based on 2-fluorobutane that is put into the still. The extracted 2-fluorobutane may be stored, and added to the next batch (i.e., recycled).

The nitrogen content in the 2-fluorobutane according to one embodiment of the invention is preferably 100 ppm by volume or less, and more preferably 80 ppm by volume or less. The oxygen content in the 2-fluorobutane according to one embodiment of the invention is preferably 50 ppm by volume or less, and more preferably 30 ppm by volume or less.

Water included in 2-fluorobutane may be removed using a normal method such as a method that brings 2-fluorobutane into contact with an adsorbent.

A molecular sieve, alumina, or the like may be used as the adsorbent. It is preferable to use a molecular sieve 3A when drying a monofluorohydrocarbon or a difluorohydrocarbon such as 2-fluorobutane or 2,2-difluorobutane (see JP-A-2014-24785 (Japanese Patent Application No. 2012-165797)). Note that a molecular sieve having a large pore size (e.g., molecular sieve 4A and molecular sieve 5A) has a drawback in that the 2-fluorobutane molecules may enter the pores, and the effect of reducing the water content may decrease, and an alkaline molecular sieve has a drawback in that 2-fluorobutane may undergo a dehydrofluorination reaction.

When using alumina, it is preferable to use activated alumina that has low crystallinity and is produced by subjecting alumina hydrate to thermal dehydration.

It is preferable to activate the adsorbent (e.g., molecular sieve or alumina) by calcination or the like before bringing 2-fluorobutane into contact with the adsorbent, since the adsorbent can adsorb a larger amount of water. The water content in 2-fluorobutane can be reduced to 50 ppm by volume or less by bringing 2-fluorobutane into contact with the adsorbent. If the water content is high, water may adhere to (remain on) the processing target surface of a substrate after etching, and delamination of a laminate film may occur when forming a copper wire or the like, or the embedded wire may be corroded. Therefore, it is preferable to reduce the water content as much as possible.

Therefore, the water content in the 2-fluorobutane according to one embodiment of the invention is preferably 50 ppm by volume or less, and more preferably 20 ppm by volume or less.

When 2-fluorobutane is stored in a container in a state in which 2-fluorobutane includes particles derived from a molecular sieve used for the water removal step, a decrease in purity may occur with the passage of time. In order to suppress a decrease in the purity of 2-fluorobutane within a container, it is preferable that the 2-fluorobutane according to one embodiment of the invention include microparticles having a size of 0.1 μm or more in a number equal to or less than 50 per ml. Therefore, it is preferable to filter and collect 2-fluorobutane after bringing 2-fluorobutane into contact with a molecular sieve in the water removal step.

As described above, it is possible to obtain high-purity 2-fluorobutane that is suitable as a plasma reaction gas by performing the step that rectifies the crude 2-fluorobutane included in the crude reaction product to have a purity of 99.9% by volume or more and a butene content of 1,000 ppm by weight or less, performing the step that removes water by bringing the resulting 2-fluorobutane into contact with the adsorbent, and performing the step that subjects the resulting 2-fluorobutane to simple distillation to reduce the nitrogen content and the oxygen content in the 2-fluorobutane to 100 ppm by volume or less and 50 ppm by volume or less, respectively.

It is possible to improve processing stability during dry etching that utilizes 2-fluorobutane by thus reducing the impurity content in 2-fluorobutane.

The 2-fluorobutane according to one embodiment of the invention is useful as a dry etching gas for dry-etching a silicon nitride film, a silicon oxynitride film, a titanium nitride film, and the like.

It is possible to efficiently and selectivity etch a silicon nitride film, a silicon oxynitride film, or a silicon nitride film that covers a silicon oxide film formed on a workpiece by utilizing a process gas that includes the high-purity 2-fluorobutane according to one embodiment of the invention when implementing a plasma etching method under plasma conditions using a process gas.

EXAMPLES

The invention is further described below by way of examples. Note that the scope of the invention is not limited to the following examples. The unit "%" refers to "wt %" unless otherwise indicated.

The following analysis conditions were used in the examples.
(1) Gas chromatography analysis (GC analysis)
Device: HP-6890 manufactured by Agilent Technologies
Column: Inert Cap-1 manufactured by GL Sciences Inc. (length: 60 m, inner diameter 0.25 mm, thickness: 1.5 μm)
Column temperature: held at 40° C. for 10 minutes, heated to 240° C. at 20° C./min, and held at 240° C. for 10 minutes
Injection temperature: 200° C.
Carrier gas: nitrogen
Split ratio: 100/1
Detector: FID
(2) Identification of impurities (gas chromatography-mass spectrometry)
GC device: HP-6890 manufactured by Agilent Technologies
Column: Inert Cap-1 manufactured by GL Sciences Inc. (length: 60 m, inner diameter 0.25 mm, thickness: 1.5 μm)
Column temperature: held at 40° C. for 10 minutes, heated to 240° C. at 20° C./min, and held at 240° C. for 10 minutes
MS device: 5973 NETWORK manufactured by Agilent Technologies
Detector: EI (accelerating voltage: 70 eV)
(3) $^1$H-NMR analysis and $^{19}$F-NMR analysis
Device: JNM-ECA-400 manufactured by JEOL Ltd. (400 MHz)
(4) Measurement of nitrogen content and oxygen content (gas chromatography)
GC device: HP-7890 manufactured by Agilent Technologies
Column: HP-5 manufactured by Agilent Technologies (length: 30 m, inner diameter 0.32 mm, thickness: 0.25 μm)
Column temperature: held at 40° C. for 5 minutes, heated to 65° C. at 5° C./min, and held at 65° C. for 1 minute
Gas sampler: 50° C.
Carrier gas: helium
Detector: TCD+pulse discharge detector
(5) Measurement of water content (FT-IR)
IG-1000 manufactured by Otsuka Electronics Co., Ltd.
Cell length: 10 m Production Example 1

A 500 ml glass reactor equipped with a stirrer and a Dimroth condenser was charged with 116 g of spray-dried potassium fluoride (manufactured by Aldrich), 137 g of 2-bromobutane (manufactured by Tokyo Chemical Industry Co., Ltd.), and 200 ml of propylene glycol. The mixture was subjected to a nitrogen atmosphere. The reactor was immersed in an oil bath, and heated at 95 to 100° C. for 12 hours. A refrigerant (cooled to −10° C.) was circulated through the Dimroth condenser After lowering the temperature of the oil bath to 80° C., two glass traps immersed in a dry ice-ethanol bath were connected to the reactor in series. A pressure controller and a vacuum pump were connected to the outlet of the glass trap. The vacuum pump was operated, and the pressure inside the system was lowered stepwise to 50 to 45 kPa, 35 to 30 kPa, and 30 to 25 kPa using the pressure controller to collect a volatile component into the glass trap. The contents of the two glass traps were combined, and analyzed by gas chromatography. It was found that the mixture included (E)-2-butene (0.71 area % (vol %)), (Z)-2-butene (0.68 area % (vol %)), 2-fluorobutane (21.23 area % (vol %)), and 2-bromobutane (77.35 area % (vol %)).

Production Example 2

A 500 ml glass reactor equipped with a dropping funnel was charged with a stifling bar, and then was charged with 44 g of 2-butanol and 200 ml of dry 1,2-dichloroethane. The mixture was subjected to a nitrogen atmosphere. The reactor was cooled with ice water, and 164 g of a hexafluoropropene-diethylamine complex (manufactured by Tokyo Chemical Industry Co.,Ltd.) dissolved in 120 ml of dry 1,2-dichloroethane was added dropwise to the mixture from the dropping funnel over about 1 hour. After the dropwise addition, the mixture was stirred for 3 hours while maintaining the reactor at 0° C., and then stirred at room temperature (25° C.) for 2 hours. After confirming by gas chromatography that the raw material had almost disappeared, ice water was added to the reaction mixture, and the mixture was washed with a 10% potassium carbonate aqueous solution and a saturated sodium chloride solution, and dried over anhydrous magnesium sulfate.

The resulting 1,2-dichloroethane solution was subjected to simple distillation to collect 31.9 g of a liquid in a receiver immersed in a dry ice-ethanol bath. The liquid was analyzed by gas chromatography and gas chromatography-mass spectrometry. It was found that the liquid was a mixture including 1-butene (2.36 area % (vol %)),(E)-2-butene (19.45% by area (volume)), (Z)-2-butene (16.78 area % (vol %)), 2-fluorobiitane (58.51 area % (vol %)), and 1,2-dichloroethane (solvent) (2.9 area % (vol %)).

Example 1

(1) Primary distillation: A still was charged with 4,340 g of crude 2-fluorobutane obtained by repeating the reaction of Production Example 1, and distillation was performed using a KS rectifying column (manufactured by Toka Seiki Co., Ltd., column length: 30 cm, packing material: Heli Pack No. 1). A refrigerant (−5° C.) was circulated through a condenser. After heating the still to 90° C., the inside of the system was stabilized by effecting total reflux for 1 hour, and a fraction was extracted at a reflux ratio of 30:1. The still was appropriately heated from 90° C. to 125° C. while observing the degree of reflux using the condenser. The resulting fraction was analyzed by gas chromatography. It was found that the fraction included 648 g of 2-fluorobutane (93.24 area % (vol %)), and included 1-butene (1.47 area % (vol %)), (E)-2-butene (1.98 area % (vol %)), and (Z)-2-butene (2.48 area % (vol %)) as impurities.

(2) Secondary distillation: A still was charged with 648 g of the crude 2-fluorobutane obtained by the primary distillation, and distillation was performed using a KS rectifying column (manufactured by Toka Seiki Co., Ltd., column length: 60 cm, packing material: Heli Pack No. 1). A refrigerant (−10° C.) was circulated through a condenser, and total reflux was effected for about 1 hour. The still was heated at 45 to 70° C. while observing the temperature of the top part of the column and the amount of the crude 2-fluorobutane remaining in the still. A fraction was then extracted at a reflux ratio of 45:1 to 15:1. The resulting fraction included 498 g of 2-fluorobutane (99.952 area % (vol %)), and included 1-butene (53.4 ppm by area (volume)), (E)-2-butene (57.8 ppm by area (volume)), and (Z)-2-butene (85.0 ppm by area (volume)) as impurities.

Spectral data of 2-fluorobutane $^1$H-NMR (CDCl$_3$, TMS) δ (ppm): 0.88 (t, 3H), 1.17 (dq, 3H), 1.73 (m, 2H), 4.35 (m, 1H)

$^{19}$F-NMR (CDCl$_3$, CFCl$_3$) δ (ppm): −173 (m, F)

Example 2

A 1.2 L SUS316 container (provided with an electropolished inner surface) charged with 100 g of a molecular sieve 3A (manufactured by Wako Pure Chemical Industries, Ltd.) was charged with 498 g of the 2-fluorobutane obtained in Example 1, and the mixture was allowed to stand at room temperature for 22 hours.

A simple distillation apparatus (in which a short column, a condenser, and a receiver were provided over a SUS316 still (capacity: 1 L)) was provided, and cooling water (−10° C.) was circulated through the condenser. 427 g of the 2-fluorobutane from which water had been removed was put into the still, and the still was heated to 50° C.

The nitrogen content mid the oxygen content in the 2-fluorobutane (determined by gas chromatography) were 515 ppm by volume and 138 ppm by volume, respectively. The simple distillation operation was terminated when about 30 wt % of the 2-fluorobutane had been extracted into the receiver, and the still was cooled to room temperature. A 1 L manganese steel cylinder (inner surface roughness: 1S) equipped with a diaphragm-type valve was charged with 309 g of the 2-fluorobutane contained in the still. The nitrogen content, the oxygen content, and the water content in the 2-fluorobutane were determined, and found to be 68 ppm by volume, 20 ppm by volume, mid 16 ppm by volume, respectively.

Example 3

A still was charged with 2,060 g of crude 2-fluorobutane obtained by repeating the reaction of Production Example 1, and distillation was performed using a KS rectifying column (manufactured by Toka Seiki Co., Ltd., column length: 60 cm, packing material: Heli Pack No. 1). A refrigerant (−10° C.) was circulated through a condenser, and total reflux was effected for about 1 hour. The still was heated from 90° C. to 125° C. while observing the temperature of the top part of the column and the amount of the crude 2-fluorobutane remaining in the still. A fraction was then extracted at a reflux ratio of 30:1 to 15:1. The resulting fraction included 309 g of 2-fluorobutane (99.903 area % (vol %)), and included 1-butene (108 ppm by area (volume)), (E)-2-butene (378 ppm by area (volume)), and (Z)-2-butene (362 ppm by area (volume)) as impurities.

Example 4

A 1.2 L stainless steel container was charged with 309 g of the 2-fluorobutane obtained in Example 3, and 60 g of a molecular sieve 3A (manufactured by Wako Pure Chemical Industries, Ltd.), and the mixture was allowed to stand at room temperature for 20 hours. The stainless steel container was connected to a 1 L manganese steel cylinder through a stainless steel tube, and the cylinder was charged with the 2-fluorobutane through a metal filter having a pore size of 0.2 μm. The cylinder was cooled with ice water, and about 30 g of the 2-fluorobutane was extracted under a pressure of 5 to 10 kPa while reducing the pressure using a vacuum pump through a pressure controller. The 2-fluorobutane was returned to room temperature, and allowed to stand for a while, and the nitrogen content, the oxygen content, and the water content in the 2-fluorobutane were determined, and found to be 36 ppm by volume, 18 ppm by volume, and 44 ppm by volume, respectively.

Example 5

A still was charged with 604 g of crude 2-fluorobutane obtained by repeating the reaction of Production Example 2, and distillation was performed using a KS rectifying column (manufactured by Toka Seiki Co., Ltd., column length: 60 cm, packing material: Heli Pack No. 1). A refrigerant (−10° C.) was circulated through a condenser, and total reflux was effected for about 1 hour. The still was heated at 45 to 70° C. while observing the temperature of the top part of the column and the amount of the crude 2-fluorobutane remaining in the still. A fraction was then extracted at a reflux ratio of 10:1. The resulting fraction included 282 g of 2-fluorobutane (99.892 area %). The fraction also included 1-butene (223 ppm by area (volume)), (E)-2-butene (516 ppm by area (volume)), and (Z)-2-butene (551 ppm by area (volume)) as impurities. A cylinder was charged with 230 g of the 2-fluorobutane in the same manner as in Example 4. The nitrogen content, the oxygen content, and the water content in the 2-fluorobutane were determined, and found to be 40 ppm by volume, 11 ppm by volume, and 26 ppm by volume, respectively.

Example 6

Dry etching evaluation: A wafer on which a silicon nitride film was formed, and a wafer on which a silicon oxide film was formed, were etched separately. The etching rate of the silicon nitride film and the etching rate of the silicon oxide film were measured, and the selectivity ratio (SiN film/SiO$_2$ film) was calculated from the ratio of the etching rate of the silicon nitride film to the etching rate of the silicon oxide film.

Specifically, the wafer on which a silicon nitride film was formed, or the wafer on which a silicon oxide film was formed, was placed in an etching chamber of a parallel plate-type plasma etching apparatus. After evacuating the system, the silicon nitride film or the silicon oxide film was etched under the following etching conditions using the 2-fluorobutane obtained in Example 2. The results are shown in Table 1.

Etching Conditions

Mixed gas pressure: 6.7 Pa

Power supplied to upper electrode from high-frequency power supply: 200 W
Power supplied to lower electrode from high-frequency power supply: 100 W
Interval between upper electrode and lower electrode: 50 mm
Electrode temperature: 20° C.
Gas flow rate
$O_2$ gas: 60 sccm
2-Fluorobutane: 50 sccm
Etching time: 180 sec Example 7

Etching results were evaluated in the same manner as in Example 6, except that the 2-fluorobutane obtained in Example 4 was used.

Comparative Example 1

Etching results were evaluated in the same manner as in Example 6, except that the 2-fluorobutane obtained in Example 5 was used. The results are shown in Table 1.

TABLE 1

| | Etching rate (nm/min) | | Selectivity |
|---|---|---|---|
| | SiN film | $SiO_2$ film | ($SiN/SiO_2$) |
| Example 6 | 25 | Not etched | Infinity |
| Example 7 | 23 | Not etched | Infinity |
| Comparative Example 1 | Not etched due to deposition | Not etched | — |

Example 8

A 2 L SUS316 container (provided with an electropolished inner surface) was charged with 900 g of 2-fluorobutane (purity: 99.924 vol %) obtained by repeating the purification by distillation of Example 1, and including 1-butene (92 ppm by area (volume)), (E)-2-butene (361 ppm by area (volume)), and (Z)-2-butene (307 ppm by area (volume)) as impurities. The container was connected to a polytetrafluoroethylene filter (manufactured by Pall Corporation, pore size: 0.05 µm), and a cylindrical stainless steel column (that had been charged with 45 g of a molecular sieve 3A ("ZEOLUM (registered trademark) A-3" manufactured by Tosoh Corporation)) so that the 2-fluorobutane that has been discharged from the container returns to the container through the column (charged with the molecular sieve) and the filter. The 2-fluorobutane included in the container was circulated and dried at 0.1 l/min for 12 hours using a pump. The water content in the resulting (dried) 2-fluorobutane was 9 ppm by volume.

The SUS316 container including the 2-fluorobutane having a water content of 9 ppm by volume was cooled to 5° C., allowed to stand for 3 hours, and connected to a liquid-borne particle counter (consisting of a light-scattering liquid-borne particle detector "KS-40A", a particle counter "KE-40", and a pressure sampler manufactured by RION Co., Ltd. installed in a clean booth) through a valve. The 2-fluorobutane was supplied at 10 ml/min. and the number of microparticles included in the 2-fluorobutyane was measured. It was found that the number of microparticles having a size of 0.1 µm or more included in the 2-fluorobutane was 37 per ml.

The invention claimed is:

1. A method of etching, comprising selectively etching silicon nitride in the presence of silicon oxide using a high-purity 2-fluorobutane having a purity of 99.9 vol % or more butene content of 1,000 ppm by volume or less, a nitrogen content of 100 ppm by volume or less and an oxygen content of 50 ppm by volume or less as a dry etching gas.

2. The method according to claim 1, wherein the high-purity 2-fluorobutane has a water content of 50 ppm by volume or less.

3. The method according to claim 1, wherein the high-purity 2-fluorobutane includes microparticles having a size of 0.1 µm or more in a number equal to or less than 50 per ml.

* * * * *